United States Patent
Wegrzyn et al.

(10) Patent No.: US 11,756,687 B2
(45) Date of Patent: Sep. 12, 2023

(54) METHOD AND SYSTEM FOR ASSESSING PERFORMANCE

(71) Applicant: Motionize Israel Ltd., Tel Aviv-Jaffa (IL)

(72) Inventors: Yoav Wegrzyn, Herzliya (IL); Eran Amit, Pardes Hanna-Karkur (IL); Hilit Maayan, Kfar Yedidya (IL); Eyal Drori, Tel Aviv (IL); Steve Barrett, Hull (GB); Amir Zviran, Tel Aviv (IL)

(73) Assignee: MOTIONIZE ISRAEL LTD., Tel Aviv-Jaffa (IL)

( * ) Notice: Subject to any disclaimer, the term of this patent is extended or adjusted under 35 U.S.C. 154(b) by 0 days.

(21) Appl. No.: 17/567,224

(22) Filed: Jan. 3, 2022

(65) Prior Publication Data
US 2022/0415515 A1      Dec. 29, 2022

Related U.S. Application Data

(60) Provisional application No. 63/215,473, filed on Jun. 27, 2021.

(51) Int. Cl.
| | |
|---|---|
| *A61B 5/11* | (2006.01) |
| *G16H 50/30* | (2018.01) |
| *G01P 13/00* | (2006.01) |
| *G06F 30/20* | (2020.01) |

(52) U.S. Cl.
CPC .............. *G16H 50/30* (2018.01); *G01P 13/00* (2013.01); *G06F 30/20* (2020.01)

(58) Field of Classification Search
CPC .......... G16H 50/30; G06F 30/20; G01P 13/00
See application file for complete search history.

(56) References Cited

U.S. PATENT DOCUMENTS

| | | |
|---|---|---|
| 11,006,860 B1 | 5/2021 | Amit et al. |
| 2004/0044440 A1 | 3/2004 | Takenaka |
| 2007/0135264 A1* | 6/2007 | Rosenberg ............... G09B 7/02 482/8 |

(Continued)

OTHER PUBLICATIONS

Robert Wood, "Arrowhead Agility Drill Test" 2008, Topend Sports Website, https://www.topendsports.com/testing/tests/arrowhead-agility-drill.htm, Accessed Aug. 19, 2022 (Year: 2008).*

(Continued)

*Primary Examiner* — John E Breene
*Assistant Examiner* — Christine Y Liao
(74) *Attorney, Agent, or Firm* — The Roy Gross Law Firm, LLC; Roy Gross

(57) ABSTRACT

A computerized method performed by a processor, an apparatus and a computer program product the method comprising: receiving a model associating motion parameters of an action performed by a subject with a score, the model based at least partially on data obtained in a controlled environment while performing a task on a first time period; determining action parameters during motion of the subject within an uncontrolled environment on a second time period; and providing the action parameters to the model, to obtain an assessment of an expected score for the subject performance of the task as would be performed by the subject in the controlled environment.

14 Claims, 11 Drawing Sheets

(56) References Cited

U.S. PATENT DOCUMENTS

| | | | |
|---|---|---|---|
| 2011/0270135 A1* | 11/2011 | Dooley | G16H 50/30 |
| | | | 600/595 |
| 2013/0244211 A1 | 9/2013 | Dowling et al. | |
| 2019/0009133 A1 | 1/2019 | Mettler May | |
| 2019/0320944 A1 | 10/2019 | Vaidyanathan et al. | |
| 2020/0129106 A1 | 4/2020 | Arbel et al. | |
| 2020/0229762 A1 | 7/2020 | Gad et al. | |
| 2021/0059565 A1* | 3/2021 | Morris | A61B 5/4088 |
| 2021/0315486 A1* | 10/2021 | Delp | G16H 50/50 |

OTHER PUBLICATIONS

Dos'Santos et al., (2018) Between-Session Reliability of Isometric Midthigh Pull Kinetics and Maximal Power Clean Performance in Male Youth Soccer Players Journal of Strength and Conditioning Research 32(12): 3364-3372.

* cited by examiner

METHOD AND SYSTEM FOR ASSESSING PERFORMANCE

CROSS-REFERENCE TO RELATED APPLICATION

This application is a continuation of and claims the benefit of U.S. Provisional Patent Application No. 63/215,473, filed Jun. 27, 2021, entitled "Scoring system to monitor and improve player performance" which is hereby incorporated by reference in its entirety without giving rise to disavowment.

TECHNICAL FIELD

The present disclosure relates to a method and system for monitoring the physical performance of subjects, such as but not limited to sport players.

BACKGROUND

Performance monitoring of individuals is a key element in the field of health monitoring for the general population, as well as coaching and personal improvement for individuals such as sports players. Professionals such as physicians, physiotherapists, or coaches monitor the performance of subjects to assess the subjects' skills, performance, technical and tactical abilities, and devise treatments plans, training techniques and game strategies.

Proper understanding of the behavior of a subject may have implications on the subject's performance, injury prevention and rehabilitation, along with specific abilities such as sport mastery. For people with disabilities or difficulties, analyzing the human biomechanics can aid in understanding the causes, possibilities, corrective actions or other aspects of healthcare.

BRIEF SUMMARY

One exemplary embodiment of the disclosed subject matter is a computer-implemented method comprising: receiving a model associating motion parameters of an action performed by a subject with a score, the model based at least partially on data obtained in a controlled environment while performing a task on a first time period; determining action parameters during motion of the subject within an uncontrolled environment on a second time period; and providing the action parameters to the model, to obtain an assessment of an expected score for the subject performance of the task as would be performed by the subject in the controlled environment. The method can further comprise estimating an aggregate score for the subject performance of a plurality of actions during the second time period. The method can further comprise estimating a potential score for the subject performance of the task in the controlled environment. Within the method, determining the action parameters during motion optionally comprises: obtaining kinematic raw data of the subject; detecting at least one stride within the motion based on the kinematic raw data; classifying the at least one stride to obtain a stride class; identifying a sequence of strides complying with a stride class combination; and determining the action parameters in accordance with the kinematic raw data associated with the sequence of strides. Within the method, the score optionally comprises a quality measure. Within the method, the quality measure optionally relates to an effort by the subject, wherein a lower effort indicates higher quality. Within the method, the score optionally comprises one or more measures selected from the group consisting of: power, agility, first step, sprint, speed, jump, endurance and ball control. Within the method, the action is optionally at least one item selected from the group consisting of: turn, jump, accelerate, decelerate, running at constant speed, cut off, maximal speed. Within the method, the task is optionally a drill selected from the group consisting of: Arrowhead, 5-0-5, T-test, lane agility, CMJ, CMJ with arms, pogo jumps, standing vertical leap, max vertical leap, 20 m sprint, 30 m sprint, 40 m sprint, 3-quarter sprint, shuttle run, MAS test, Yo-Yo, and 30-15. Within the method, the expected score is optionally a measure of the task based on at least one metric selected from the group consisting of: completion time, segment time, distance, frequency, maximal velocity, symmetry, height and weight. Within the method, the task is optionally a combination of one or more actions selected from the group consisting of: walking, turning, climbing stairs, sitting and rising, and the score is stability or neurological condition. Within the method, the measurement apparatus is optionally wearable IMU unit, video capture system or force sensor. The method can further comprise generating the model, optionally comprising: obtaining kinematic raw data of one or more subjects; detecting one or more strides within the motion based on the kinematic raw data; classifying each strides to obtain a stride class; identifying an action comprising a sequence of strides complying with a stride class combination; obtaining a label for the action; and providing action parameters retrieved from the raw data associated with the sequence of strides and the label to a model trainer, to obtain the model. Within the method, the task is optionally a predetermined drill and the expected score is optionally a time a subject is expected to complete a drill. Within the method, the score is optionally agility, the actions are optionally turns, the controlled-environment tasks are optionally arrowhead and 5-0-5 cod drills, and the drill time is optionally indicative of agility of the subject.

Another exemplary embodiment of the disclosed subject matter is a computer-implemented method comprising: receiving a model associating motion parameters of an action performed by a plurality of individuals with a time, the model based at least partially on data obtained in a controlled environment on a first time period; determining action parameters during motion of a subject within an uncontrolled environment on a second time period; and providing the action parameters to the model, to obtain an assessment of an expected time for the subject performance of the action in the controlled environment.

Yet another exemplary embodiment of the disclosed subject matter is a computer-implemented method comprising: receiving a model associating values of two motion parameters of an action performed by a subject with a score; displaying the model in a graphic representation having two dimensions, wherein the two dimensions of the graphic representation are related to the two motion parameters, and the score is indicated as color or pattern, wherein the model is based at least partially on data obtained in a controlled environment on a first time period, and wherein the model is further adapted to represent data points obtained in an uncontrolled environment on a second time period, the second time period later than the first time period; and displaying the model over a display device. Within the computerized method, the graphic representation is optionally a polar coordinate system, wherein a radius of the polar coordinate system optionally represents speed, an angle of the polar coordinate system optionally represents a turning angle, and color or pattern optionally represents motion quality or time. The method can further comprise indicating on the model a point representing an action performed in an uncontrolled environment, wherein the color or pattern associated with an area containing the point indicates a score of the action.

Yet another exemplary embodiment of the disclosed subject matter is an apparatus having a processor, the processor being adapted to perform the steps of: receiving a model associating motion parameters of an action performed by a subject with a score, the model based at least partially on data obtained in a controlled environment while performing a task on a first time period; determining action parameters during motion of the subject within an uncontrolled environment on a second time period; and providing the action parameters to the model, to obtain an assessment of an expected score for the subject performance of the task as would be performed by the subject in the controlled environment.

Yet another exemplary embodiment of the disclosed subject matter is a computer program product comprising a computer readable storage medium retaining program instructions, which program instructions when read by a processor, cause the processor to perform a method comprising: receiving a model associating motion parameters of an action performed by a subject with a score, the model based at least partially on data obtained in a controlled environment while performing a task on a first time period; determining action parameters during motion of the subject within an uncontrolled environment on a second time period; and providing the action parameters to the model, to obtain an assessment of an expected score for the subject performance of the task as would be performed by the subject in the controlled environment.

THE BRIEF DESCRIPTION OF THE SEVERAL VIEWS OF THE DRAWINGS

The present disclosed subject matter will be understood and appreciated more fully from the following detailed description taken in conjunction with the drawings in which corresponding or like numerals or characters indicate corresponding or like components. Unless indicated otherwise, the drawings provide exemplary embodiments or aspects of the disclosure and do not limit the scope of the disclosure. In the drawings.

DETAILED DESCRIPTION

Figure 1:
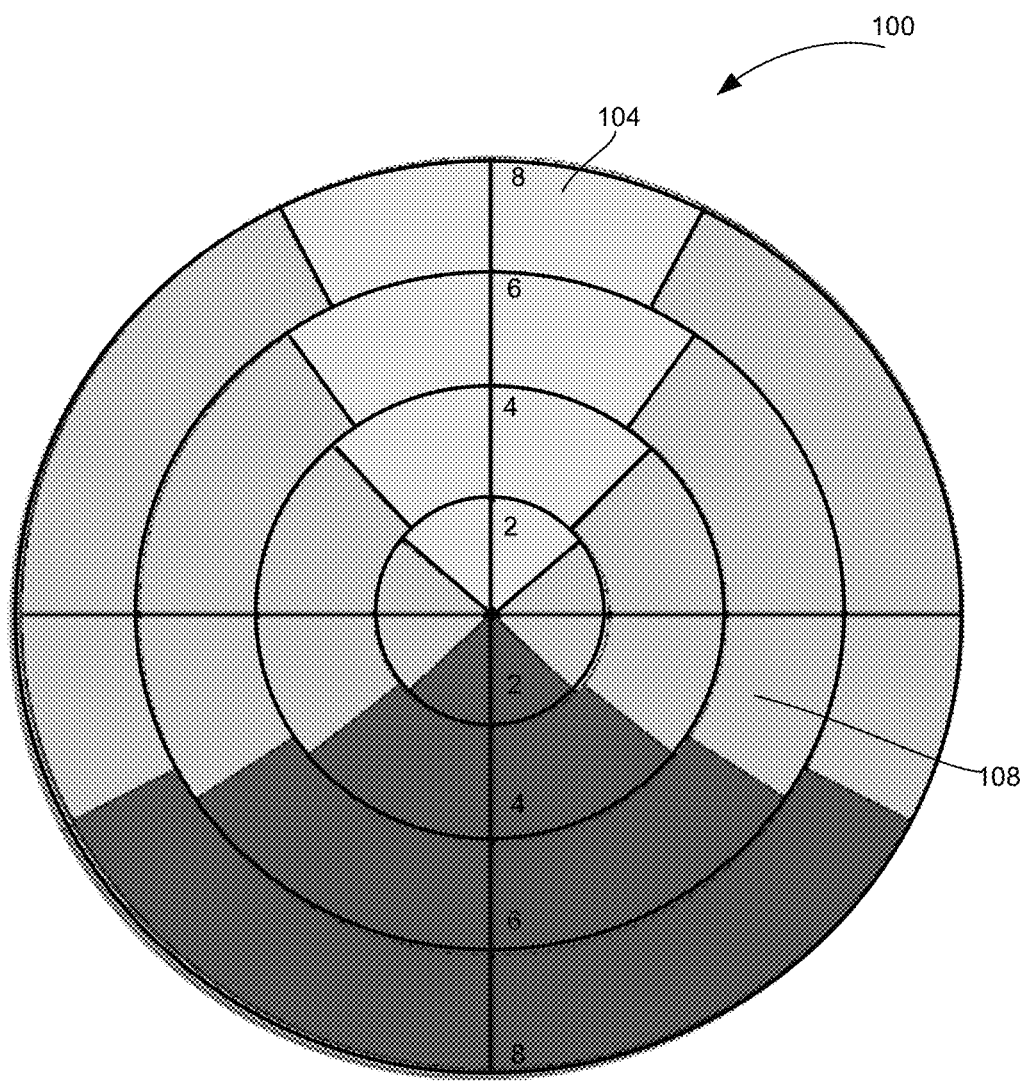
FIG. 1 is a visual representation of a model associated with a turning action, in accordance with some exemplary embodiments of the disclosed subject matter.

In the description below, unless noted otherwise, the term "stride" is to be widely construed as covering the movement of one foot during a double step, i.e., from the time the heel of one foot contacts the ground, until the same heel contacts the ground again.

In the description below, unless noted otherwise, the term "step" is to be widely construed as covering a single step, for example from the time one heel forms contact with the ground, until the second heel forms contact with the ground.

In the description below, unless noted otherwise, the terms "subject", "individual", "human subject", "user", "player", "patient", "healthcare patient" or similar terms are used interchangeably and are all to be widely construed as covering an individual whose biomechanical behavior is examined.

One technical problem handled by the disclosure relates to the need to quantify physical activity of an individual, such as a sports player, an individual healing from injury, an elder person, or the like. There is thus a need for common metrics that provide feedback, such as the performance of the individual, which can also provide for assessing the potential of the individual, monitor the individual performance over time, or the like.

Currently available methods comprise measuring motion parameters of individuals in controlled environment, for example during the performance of known drills, such as Arrowhead, 5-0-5, T-test, lane agility, CMJ, CMJ with arms, pogo jumps, standing vertical leap, max vertical leap, 20 m sprint, 30 m sprint, 40 m sprint, 3-quarter sprint, shuttle run, MAS test, Yo-Yo, and 30-15. The drill may be performed with or without possession of a ball, or under any other special conditions. The subject may perform the drills one or more times, and may repeat the drills every period of time or as otherwise required, such that the subject's performance may be monitored over time.

These measurements may be aggregated to obtain physical and technical measures that provide insights related to aspects of the activities of the individual. The physical and technical measures may include, but are not limited to, covered distance, maximal velocity, turning time, number of ball touches, step contact time, or the like. However, these measurements cannot assess scores such as but not limited to agility, power, or speed, which are required for determining training plan, gaming strategies, injury risk, or others.

A significant problem that inhibits scoring relates to collecting measurements only from controlled environments. For example, a football player may be required to repeat a specific drill over and over again, after which the player's performance may be assessed. However, such drills, although useful as a method for measuring performance, may not provide the best indication of the individual's abilities and actions which are actually performed during a real game. Moreover, repeating the drills consumes precious training time which could be used for more efficient training. Further, the drills may imitate to certain degree a certain type of actions, but may not enable the individual or the coach to exactly assess the individual's actual performance in real-life situations such as games, and thus update the training program. Additionally, controlled environments may also require specific locations and equipment, which make it further harder to obtain the measures.

Another problem relates to the lack of measures for the player's technique or the forces acting on the individual's body, which is important in order to assess the load on the individual and thus the injury risk.

Yet another problem relates to assessing the overall injury risk of an individual. This is important for patients, and in particular elderly patients, as well as to sportsmen, such that the training scheme may be adapted, and players may be selected to games while avoiding excess risk, or the like.

Determining an individual's scores presents some additional challenges. First, multiple measurements, which may be non-trivial to collect, may be required to be measured during activity, and combined for assessing one or more scores. Collecting such measurements may be harder in controlled environment than in uncontrolled environment.

Further, it may be needed to assess the actual performance vs. the potential of the individual, e.g., the measure of how the individual did in the last assessment may not be enough to realize what the individual can potentially do when needed.

Yet another problem relates to monitoring the individual's performance over time, and comparing it to other individuals, for example other team members, and to predetermined goals.

One technical solution relates to learning a model, also referred to as an Artificial Intelligence (AI) engine, such as a Neural Network (NN), a Deep Neural Network (DNN), a Recurrent Neural Network (RNN), a Long-Short Term memory, or any other AI engine, of the user's performance when performing activities in a controlled environment, for example when performing a predetermined drill. The model may be built upon a number of measurable parameters, and one or more labels for the drill. The labels may be determined automatically, or assigned by a professional, such as a physician, a coach, or the like. The labels, or a combination thereof may be associated with a particular score assigned to the performance of the drill.

For example, a common method to assess an athlete "agility" is using Arrowhead and 5-0-5 drills. In both drills the athlete has to complete a path between a cone setup as fast as possible. The agility score is determined by how fast the athlete completes the drills.

A model can be developed to predict the drills completion time based on the gait characteristics during the drills, and specifically during turns, wherein the characteristics may be received from sensors attached to the body of the athlete performing the turn. The model can be constructed based upon drills performed by a plurality of athletes. This model can be later applied on characteristics obtained during turns in an uncontrolled environment, to estimate the athlete agility skill, without performing any specific drill. The agility score from the open environment predicts the best time this athlete would be able to perform the agility drills.

In addition to a score based solely on the drill completion time, additional predictions can be provided by the model, based on the athlete turning technique. One such dimension may be the effort on the athlete's body during the turn, which may then be compared to a desired effort and/or whether or not the athlete can improve his gait pattern to turn faster.

In order to add to the model the above predictions, a reference can be created for example based on practitioners' subjective scores and/or force measurements during the turns. In further embodiments, the technique may be ranked using data obtained for past users and an AI model generated for predicting which gait pattern may lead to better completion time.

In addition to assessing the agility of a single turn, the player's overall performance may be assessed, for example over a match. In one example, the agility of the best turn of the player during the game may be selected as the score for the player. In another example, all turns, may be aggregated, by summing or averaging the scores, or the like. Additionally, the overall performance of the player may be learned, for example by examining the number of turns, the number of turns in each direction, or the like.

Another technical solution of the disclosure relates to a model that can assess the ability of the athlete to perform different turns (rather than the athlete's "agility"). Since the quality of turns can be estimated for all turning conditions, such as each combination of entry speed, exit speed and change of direction angle, the athlete's turn profile can be quantified.

The term quality may be indicative of the effort put by the individual into performing the action. It will be appreciated that a high quality action may be performed with relatively low effort by the individual, and vice versa.

When the individual later performs an activity, for example plays football, a specific sequence of strides which forms an action corresponding to the drill upon which the model was trained, for example a turn, may be identified. The parameters of the action may be obtained and provided to the engine, which may then output the predicted score, e.g., the expected time and/or quality of a turn.

The model thus predicts the score that could be expected had the user performed a controlled-environment-drill, from the parameters of an action taken as part of an activity performed in an uncontrolled environment.

The parameters may be related to the specific drill, and may therefore change from one case to the other. For example, the parameters may be the number of steps, the total change in the motion direction, the total turn duration and other characteristics of the entire turn. Additional parameters can be velocities, accelerations, contact time of the player with the ground and step durations, angles of the trunk, thigh, knee, shank, ankle and foot during different periods of the turn sequence, or ratios between the parameters in different periods. whether the player is with or without the ball, or the like.

In some embodiments, a drill may be defined as a combination of one or more actions, such as walking, turning, climbing stairs, sitting and rising, and the score may be, for example, the stability or neurological condition of the subject.

The parameters, both for training the engine and for making predictions, may be extracted from kinematic measurements of the athlete's motion. The kinematic measures may be analyzed for detecting strides. Each stride may be classified by a classifier to obtain the stride class, and a further engine may identify an action comprised of a sequence of strides of specific classes, relevant to the drill.

Once the action or drill is identified, the relevant parameters may be calculated from the kinematic measurements obtained during the action, and used as input for the AI engine (for training or predicting). Additionally or alternatively, one or more of the parameters may be estimated by applying other techniques, such as image processing, to a series of images depicting the individual at action. Another example is applying a different model designed to estimate forces from kinematic parameters of a step, and using its output parameters as additional input parameters of the model.

It will be appreciated, that determining the score is not limited to actions performed in an uncontrolled environment, and can be performed also for actions taken in a controlled environment.

Yet another technical solution relates to analyzing and aggregating the scores over a session, for example aggregating the effort put during a football match by one or more of the players. The total effort may be a predictor for a possible injury, therefore a coach may take this factor into consideration when building training plans, selecting players for a match, or the like.

Yet another technical solution relates to identifying performance trends of one or more individuals. For example, the quality of actions may be monitored for a player along a football match to check how the fatigue influences his performance, monitor the actions over a season, or the like. In another example, it may be determined that a player tends to perform actions in a particular manner, for example more right turns than left turns. It may be checked whether this is indeed the required behavior, and/or to specifically train the player to perform these actions better.

Yet another technical solution relates to comparing the performance of different players, for example using the aggregate scores over a game, a season, or the like.

Yet another technical solution relates to comparing the performance of a player in different conditions, for example while playing in different positions, using different shoes, or the like.

Yet another technical solution relates to comparing the effect of external factors on player or team performance, for example the surface on which the session was held, or the like.

Yet another technical solution of the disclosure relates to a visual presentation of the model and the scores of specific actions by a player. A two-dimensional representation may be used for representing a model based on two action parameters, which receives as a label and then outputs one score (which may be a combination of multiple other scores). The label or score may be represented as a color or pattern of the relevant area of the two-dimensional presentation.

In some embodiments, a polar representation may be used. In such representation, the angle may represent one parameter and the radius may represent another parameter. The area of the model may be divided into two or more areas having different colors or patterns, according to the label associated with each point and the training process. The different colors or patterns thus provide a visual representation of the action parameters and their corresponding scores.

By indicating on the model presentation one or more points associated with an action taken for example in an uncontrolled activity, the color or pattern applicable to the area of the model in which the point is located, provides its score.

The parameters represented by the axes may be selected upon the specific action. The parameters may relate directly to received measurements, to any of the action parameters provided to the AI engine, or other relevant parameters that may help a viewer analyze the subject's performance.

In the example above related to turns, the angle may represent the turning angle by an individual, the radius may represent the turn speed, and the different colored areas of the graph may represent the time and/or the quality/effort put by the individual into the turn.

One technical effect of the disclosure provides for using the actions performed by an individual in an uncontrolled environment, to predict the performance as it would be in a controlled environment. The prediction provides a benchmark for assessing the performance of the individual in real-life, without wasting precious training time on drills, and without requiring special equipment or location. The prediction is performed automatically using sensory data received from sensors attached to the player, with or without data obtained from analyzing images of the individual, and by feeding the data to an AI engine to obtain a prediction.

Another technical effect of the disclosure provides for efficient manner for assessing the performance over a period of time, such as a match, a season or the like, identifying trends, comparing between different individuals, or the like. The disclosure thus enables a practitioner to focus on areas requiring specific training, make better selections for a match, avoiding injuries, or the like.

Yet another technical effect of the disclosure provides for a convenient visualization of an individual's performance, including a visual representation of the baseline created for the user, and indications of the scores associated with actions performed at a later time. The visualization enables for easy decision making regarding for example training to be assigned to the individual.

In some embodiments, one or more types of actions may be indicative for assessing specific scores. For example, agility may be assessed by the speed and effort put into a drill comprising a predetermined sequence of strides, comprising forward-turn-forward sequence, i.e., changing an advancement direction.

For visualization purposes, the angle and speed of a turn may provide a convenient representation of the turn.

Although FIG. 1-FIG. 3 below refer to agility, it will be appreciated that this is merely an example, and the same methodology may be applied to any other score.

As an initial benchmark, a plurality of drills may be performed, in different manners, and one or more scores may be associated with each such drill.

Referring now to FIG. 1, showing a visual representation of a model associated with a turning action, in accordance with some exemplary embodiments of the disclosed subject matter. The representation, generally referenced 100, shows a polar coordinate system, in which the angle represents the turning angle, and the radius represents the turning speed in m/s. Thus, area 104 represents turns of 0 to about 30 degrees, at speeds ranging from 6 m/s to 8 m/s, while area 108 represents turns of about 90° to about 120°, at speeds ranging from 4 m/s to 6 m/s. It will be appreciated that each of the turn angle and the speed (or any other parameter used in the visualization) may or may not be within the parameters used for training the AI engine, but in either case, the visualization parameters may be extracted from the kinematic measurements in the same manner.

Once a plurality of turn actions is collected for example when a subject has performed predetermined drills, and a label has been associated with each such action, such as time, height effort, or others, an engine such as an AI engine may be trained upon the parameters relevant to the action, thus providing the different colored areas.

In some embodiments the scores may be assigned arbitrarily. For example, it may be determined that turns at angles of −45° to 45° are of low effort, turns at angles of −45° to −135° and 45° to 135° are of medium effort, and turns at angles of −135° to −180° and 135 to 180°, are of high effort.

In other embodiments, the scores may be assigned automatically, in accordance with a measurable size, such as time or height. In further embodiments, the scores may be assigned by an expert, such as a practitioner estimating the effort by the individual.

Once trained, the AI engine may predict the expected score for each point within the coordinate system. In other words, the training may determine the boundaries between areas having different effort levels, based on the actions provided as input.

The scores are shown in FIG. 1 by the various shades of gray, such that the higher the effort, the darker the shade. It will be appreciated that although representation 100 shows three gray levels, i.e., three effort levels, the labels and the prediction may comprise any number of labels and predictions.

The trained AI engine, which can be visually represented as shown in FIG. 1, may be regarded as a benchmark of an individual.

Therefore, different individuals or the same individual at different times, may exhibit different behaviors reflected by different predictions provided by corresponding AI engines trained upon the relevant drills.

Figure 2:
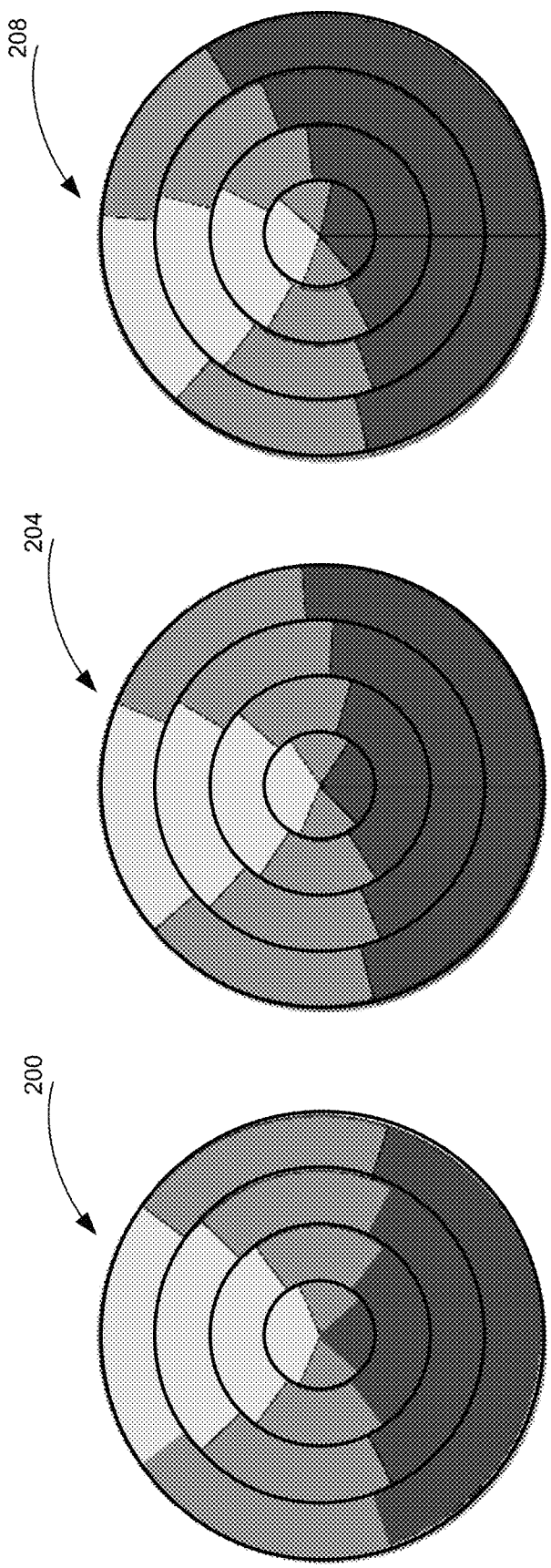
FIG. 2 shows three graphs, each representing an AI engine trained upon data from a different individual, in accordance with some exemplary embodiments of the disclosed subject matter.

Referring now to FIG. 2, showing graphs 200, 204 and 208 each representing an AI engine trained upon data from individual 1, individual 2, and individual 3, respectively.

It is seen that the light gray areas decrease in size and the dark gray areas increase in size from graph 200 to graph 204 and further from graph 204 to graph 208. Thus, individual 1 performed better than individual 2, who in turn performed better than individual 3.

Further, while graph 200 is substantially symmetric around the vertical axis, meaning that individual 1 puts the same effort in turns to the left and to the right, individual 2 puts more efforts in turns to the right, and even more so for individual 3.

Thus, a professional such as a coach may prefer to let individual 1 play for longer periods of time, as the risk injury of individual 1 may be lower than that of individual 2 and individual 3.

Further, the professional may assign more exercising on right turns to individual 2 and individual 3 than on left turns. Additionally or alternatively, if individual 2 or individual 3 suffered an injury the professional may learn that they have not completely healed and should be watched more carefully.

Figure 3:
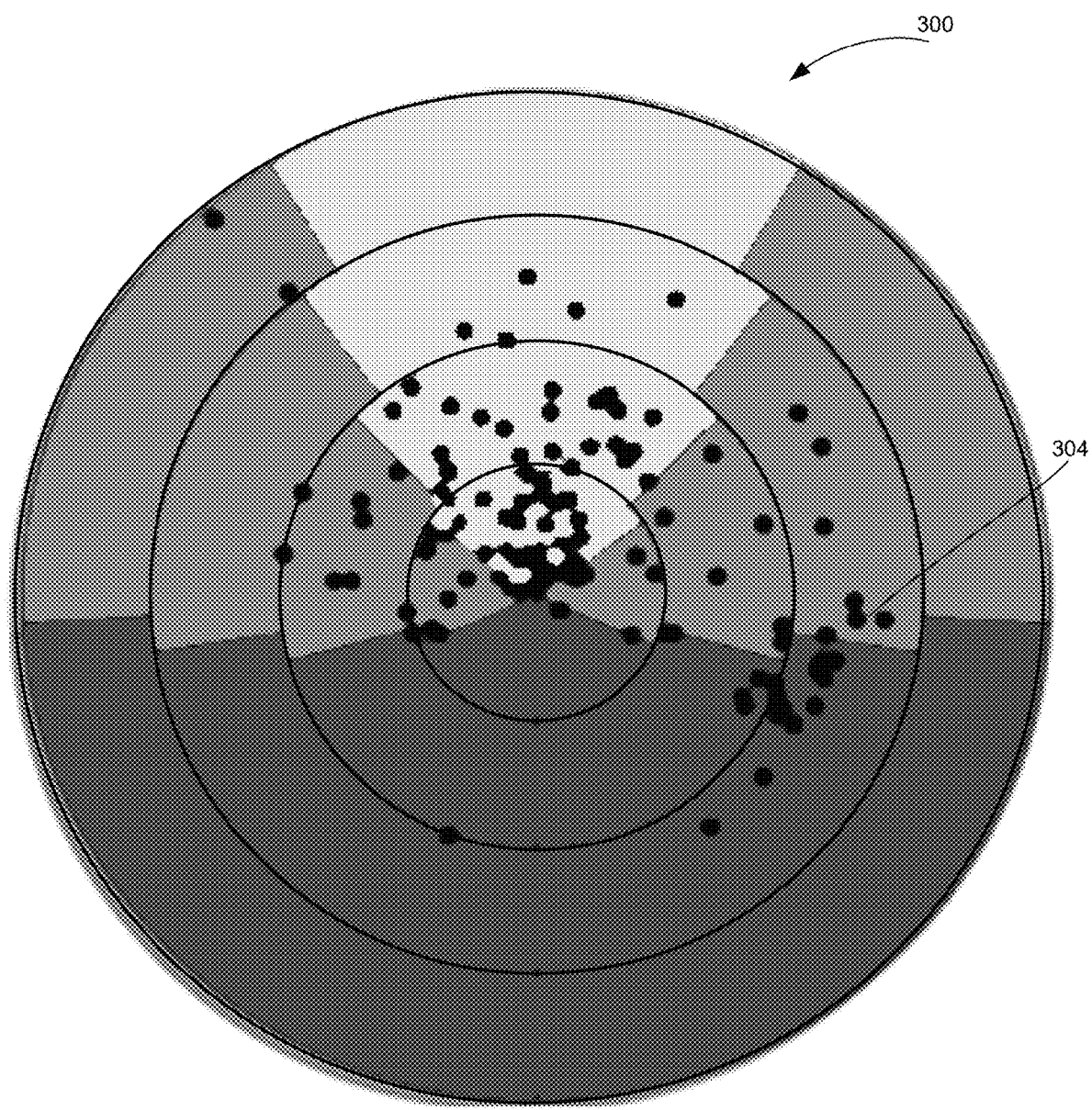
FIG. 3 is a graph indicating the areas as predicted by a trained AI engine for a particular individual, and additional points in accordance with some exemplary embodiments of the disclosed subject matter.

Referring now to FIG. 3 showing a graph 300 indicating the areas as predicted by a trained AI engine for a particular individual, similar to FIG. 1, in accordance with some exemplary embodiments of the disclosed subject matter.

Additionally, more points may be indicated on the graph, such as point 304 representing a turn of about 90° at about 4.4 m/s. The points may be determined over a period of time, such as a match or part thereof, a season of games, or the like.

Each such point thus represents a turn performed during the time period, wherein the kinematic measurements taken during the turn are used for extracting the speed and angle of the turn.

The gray level associated with the area in which the point is located thus indicates the expected effort level the individual may have had to put in for performing an equivalent drill.

Considering the collection of points, it is seen that the individual performed quite a lot more right turns at about 90° than corresponding left turns, and that these turns require quite significant effort from the individual. A practitioner considering the graph (or a corresponding representation of the data) may determine that the individual needs to practice more right turns, or that the individual is not acting as expected and should not perform so many right turns. Alternatively, this bias towards right turn may be necessitated by the individual's role.

Moreover, the practitioner may notice the overall load on the individual, calculated for example as the sum of efforts caused by the turns over the period of time. For example, each point in a light gray area may be calculated as 1 effort unit, each point in a medium gray area may be calculated as 2 effort units, and each point in a dark gray area may be calculated as 3 effort unit. Thus, 30 points in the light gray area, 25 points in the medium gray area and 10 points in the dark gray area would sum up to a load of 30*1+25*2+10*3=110 effort units.

This number may be compared to the load of the individual in other matches, showing for example how hard the individual played. This may allow the practitioners to adjust the training session loads to the match load, thereby allowing the player to be in optimal match shape. In other embodiments, the effort trend may be determined. For example, a sudden increase may indicate an injury or another problem.

In further embodiments, the load of the different turn segments can be compared and monitored.

In further embodiments, the load on different individuals may be compared, indicating which individuals are more prone to injury and should be watched more carefully.

Figure 4:
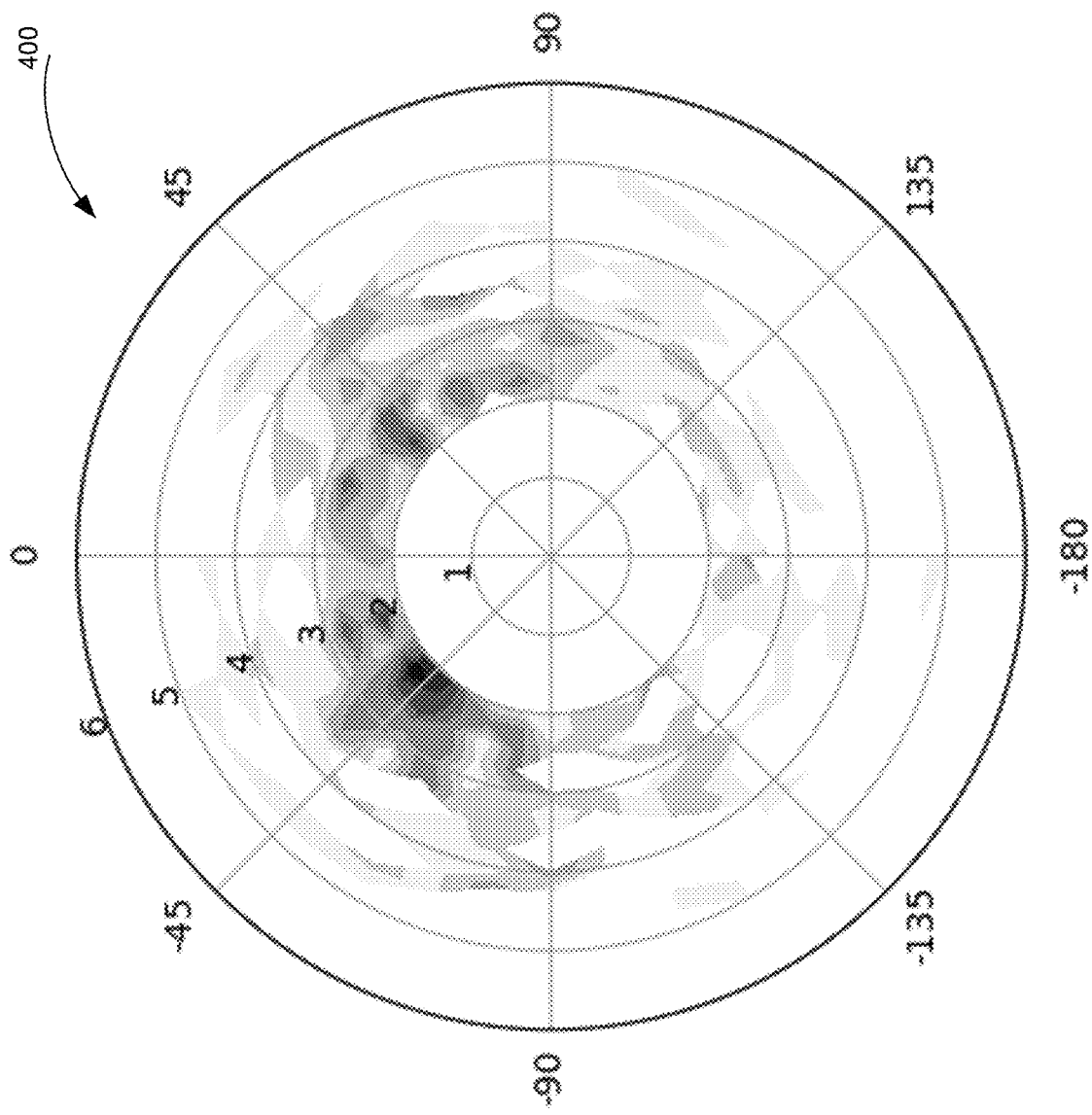
FIG. 4, FIG. 5A and FIG. 5B are visualizations of other scores, in accordance with some exemplary embodiments of the disclosed subject matter.
Figure 5A:
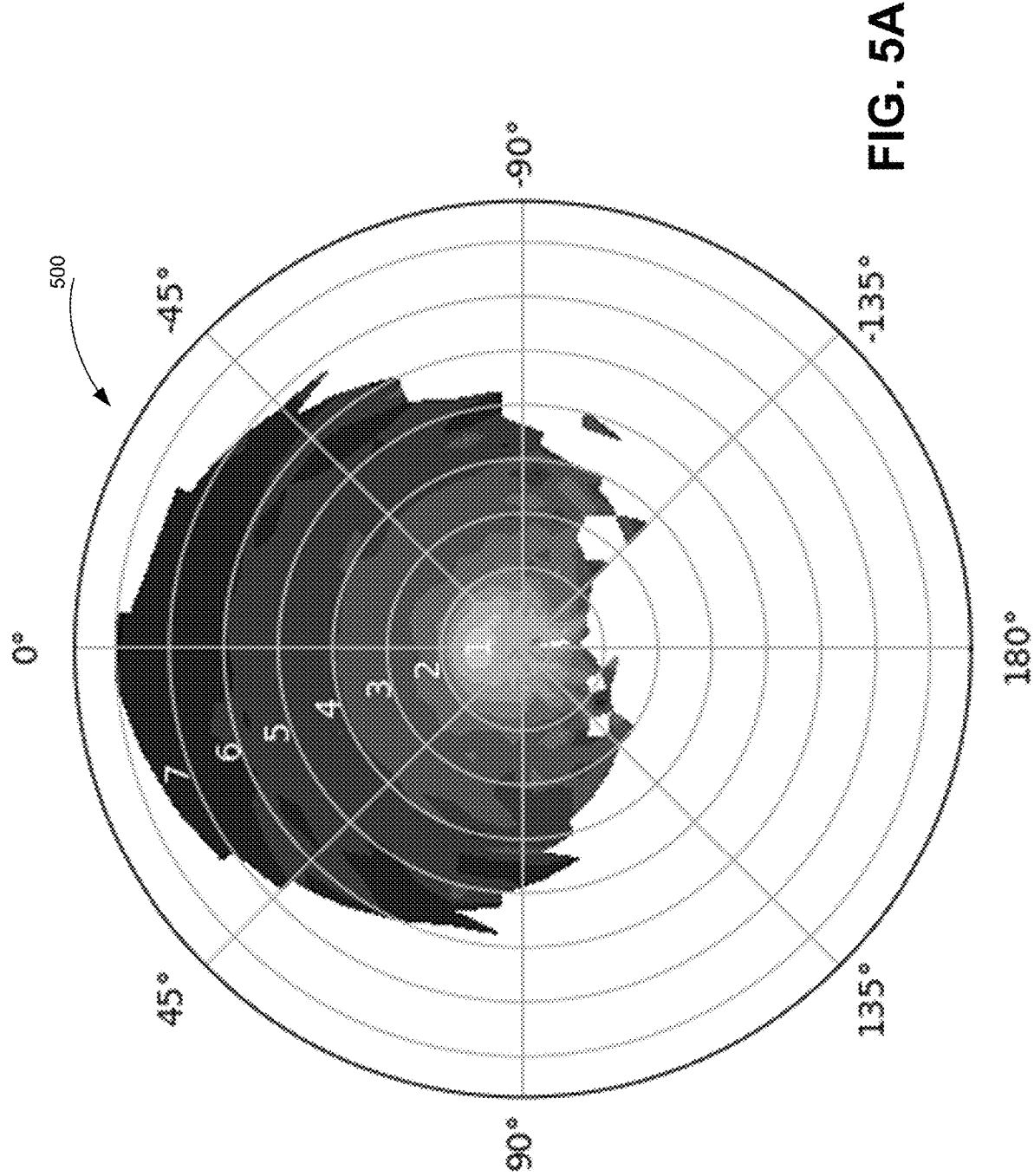
Figure 5B:
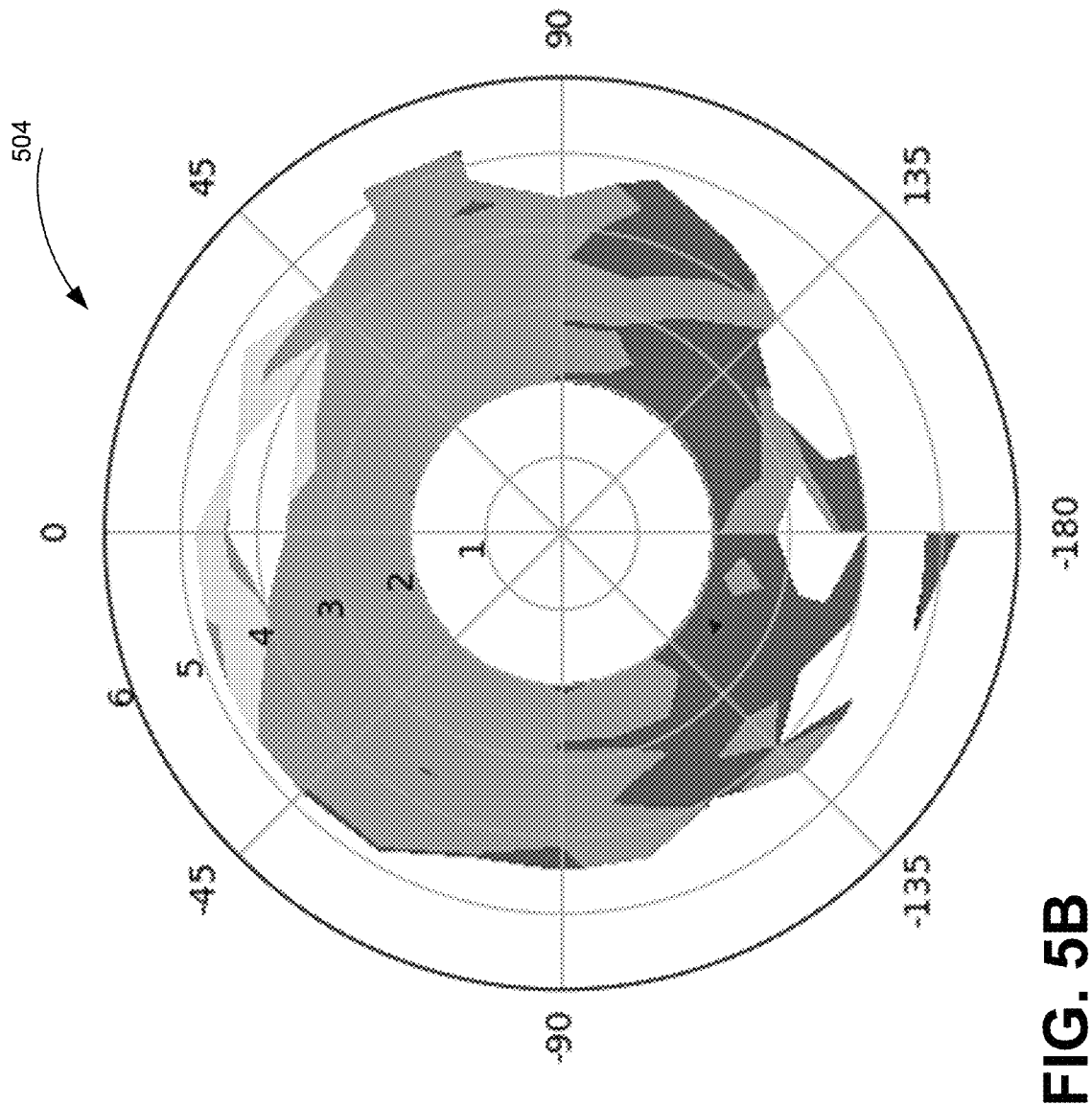

Referring now to FIGS. 4, 5A and 5B, demonstrating a visualization of other scores that can be assessed using the disclosed solution, in accordance with some exemplary embodiments of the disclosed subject matter.

FIG. 4 shows a polar coordinate system generally referenced 400, in which the angle represents the angle of a taken turn, and the radius represents the speed at the beginning of the turn. Darker color indicates higher amount of turns. It can be seen that the player to which FIG. 4 pertains, tends to take more left turn than right turns.

The engine and visualization enable a practitioner such as a coach to analyze the behavior of a player. For example, whether this turn distribution is associated with the player's performance of his role, or is the result of an injury or another problem, analyze the distribution of turns in different matches, analyze the distribution of turns relative to other players with similar roles, or the like.

FIG. 5A shows a polar coordinate system 500, in which the angle represents the angle of a taken stride, and the radius represents the stride speed. Each colored area represents the flight ratio, i.e., the part of the stride time in which both feet of the user did not touch the ground, wherein a darker color indicates a larger flight ratio. It is seen that this ratio is highest when the individual advances forward, for example at a small angle such as −30° to 30°, and at higher speeds, such as 7-8 m/s.

This representation may help to define the different intensity zones at a step level. At speed of 1 m/s there is a big variation in the flight ratio value at around 40°, showing transition to a different intensity zone.

FIG. 5B also shows a polar coordinate system 504 in which the angle represents the angle of a taken turn and the radius represents the turn speed, the color of an area provides an estimate of the turn effort. This estimator uses the total impulse during the turn, wherein the impulse may relate to the change in the player's momentum during the turn. The impulse may be used to determine the effort areas, as presented for example in FIGS. 1-3 above.

It will be appreciated that in FIGS. 4, 5A, and 5B an engine may have been trained on the parameters as obtained in a controlled environment, wherein the label and therefore the score refers to the number of turns in FIG. 4 and the effort in FIG. 5B. The visualizations shown in FIGS. 4, 5A and 5B provide a visual demonstration of the engine training results, whether it is the accumulated number of turns as in FIG. 4 or the effort as in FIG. 5B, such that if a data point having specific angle and speed is provided to the engine, the prediction would be in accordance with the accumulated number of turns or the effort, respectively.

Figure 6A:
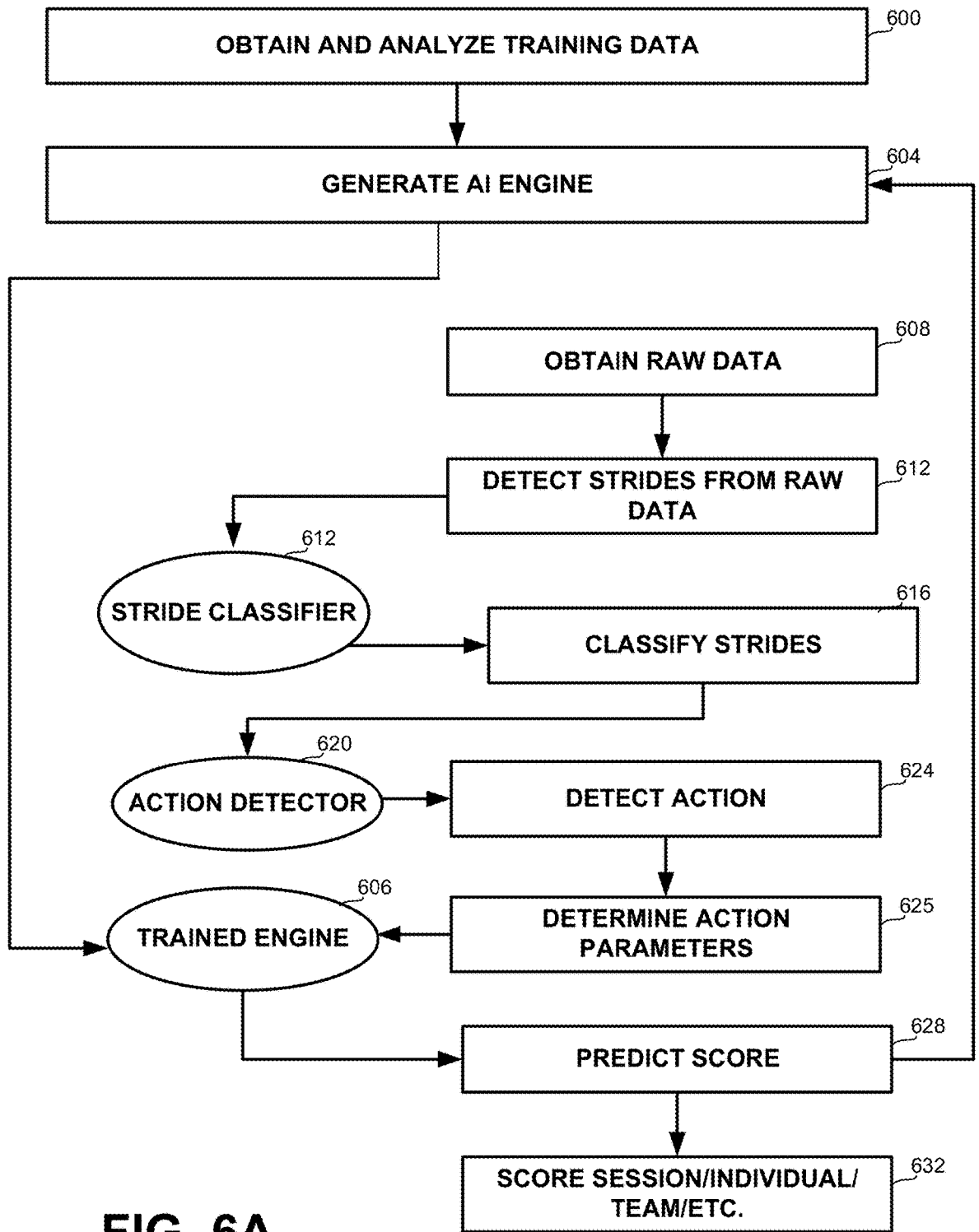
FIG. 6A is a flowchart of steps in a method for assessing performance, in accordance with some exemplary embodiments of the disclosure.

Referring now to FIG. 6A, showing a flowchart of steps in a method for assessing performance, in accordance with some exemplary embodiments of the disclosure.

On step 600 training data in controlled environment may be obtained. The training data may comprise data related to one or more subjects performing certain drills. The drills may contain actions relevant to the score object, for example agility drills contain turns. These drills may be but not limited to Arrowhead, 5-0-5, T-test, lane agility, CMJ, CMJ with arms, pogo jumps, standing vertical leap, max vertical leap, 20 m sprint, 30 m sprint, 40 m sprint, 3-quarter sprint, shuttle run, MAS test, Yo-Yo, 30-15, or the like. The data may be based on measurements taken during performance of the drills, as may be analyzed to detect strides, classify the strides and identify certain actions, such as "turn". The measurements may be collected by one or more sensors attached to the subject's body, as detailed in steps 612, 616, 624 and 625 below and in association with FIGS. 7A-7F below.

On step 604, the parameters associated with the actions may be provided together with one or more labels for each such action to generate a trained engine 606. Step 604 is further detailed in association with FIG. 6C below.

On step 608, when the engine is trained, raw data may be collected for the subject in an uncontrolled environment. The data may be obtained as detailed above, from one or more sensors attached to the subject's body.

On step 612, strides may be detected from the raw data, and on step 616 the strides may be classified by stride classifier 614. For example, the strides may be classified into one or more of the following classes: a run, walk, or jump; forward, backward, turn (left or right), side stepping (left or right), up, down, or same position; acceleration, deceleration, or constant velocity; environment specific parameters, for example ball related gaits: receive, release, dribble, or no touch; game specific motions, for example tackle.

Further details of stride detection and classification are provided in U.S. Pat. No. 11,006,860 filed Oct. 5, 2020, titled "Method and apparatus for gait analysis", incorporated herein by reference in its entirety and for all purposes.

On step 624, the strides may be further analyzed, for example by action detector 620, to obtain stride sequences characterizing a required action, such as a few steps forward, turn to the right/left, and few additional steps. Action detector 620 may thus be adapted to search and recognize such sequences.

On step 625, the action parameters relevant to the detected action may be retrieved. For example, the parameters may be retrieved from the raw data collected form the sensors attached to the subject and related to the time in which the action was performed, or from further processing thereof.

On step 628, the data relevant to the detected actions, such as parameters extracted from the raw data which relate to the strides constituting the action, may be provided to AI engine 608 trained upon the training data, to obtain a score corresponding to the label upon which the engine was trained. The parameters, which may be the same parameters used for training AI engine 606, may be specific to the action, for example the number of steps their flight and contact times, initial and final velocities, velocity ratios, whether the player is with or without the ball, or the like. Additional parameters may be added related for example to the surface and/or the athlete height, weight, leg length and the like.

The score of one or more actions may be obtained from the engine and used for further training AI engine on step 604, to update AI engine 606. For example, AI engine 606 may be re-trained every predetermined period of time, when at least a number of actions has been collected, or the like.

The score may be used as is, that is a score per action, and/or combined with further analysis results.

For example, on step 632, a single score can be provided for a period based on aggregations of all actions done within this session.

As another example, on step 632, the potential of the subject may be analyzed, rather than only the actual performance. While the score indicates how the subject would have performed the associated drill, the potential assessment may provide an indication to how the subject could have performed the drill, had the subject made his best.

The potential may be assessed by examining the behavior of the subject and comparing to baseline behaviors of the subject or of other subjects. For example, it may be determined that if the subject performed on average in the range of $[X_1 \ldots X_2]$, than the subject can do up to $1.3*X_2$. In another example, the ratio between the contact time and the speed may be determined, wherein if the contact time does not decrease, then the performance cannot be improved. In a further example, if there is a plateau in the effort graph of the subject, the subject cannot improve over that. In some embodiments, interpolation or extrapolation techniques may be employed for assessing the potential of a subject.

In another example, data for multiple data points, such as multiple turns may be aggregated over a game, a season, or the like, to assess the effort of a subject and determine a trend or an injury risk, to devise a training plan, or the like. In further embodiments, data related to two or more subjects, for example a whole team or a section thereof may be aggregated, to derive conclusions related to the team or section. In further embodiments, data aggregated for two or more subjects may be compared, in order to select the more appropriate person for a task, or reduce injury risk.

It will be appreciated that additional parameters may be added and considered in training and using the AI engine, fatigue, external conditions, e.g. surface or special equipment such as shoes, action technique specifics, change of directions vs. turns, i.e. body vs. motion direction, or the like.

Figure 6B:
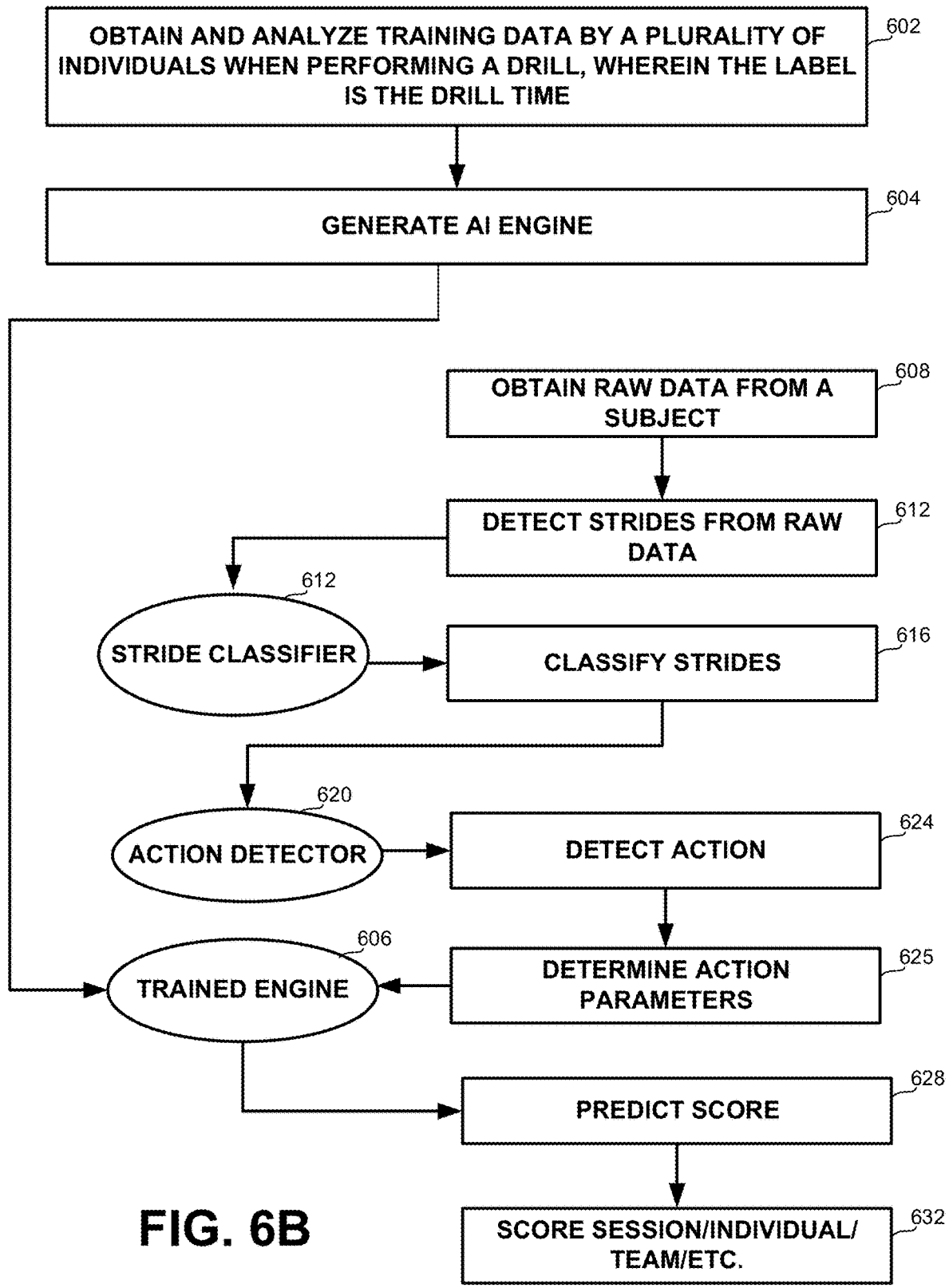
FIG. 6B is a flowchart of steps in a method for assessing a subject's agility, in accordance with some exemplary embodiments of the disclosure.

Referring now to FIG. 6B, showing a flowchart of steps in a method for assessing the agility of a subject, in accordance with some exemplary embodiments of the disclosure. The agility of a subject is related to how fast a subject may respond and change the motion direction. For example, it can be defined as how fast a subject can perform Arrowhead and 5-0-5 drills, i.e., a subject that completes the drills in a shorter period is more agile. Similarly, other scores can be defined based on performance level of other drills.

On step 602 training data may be obtained. The training data may comprise data related to a plurality of subjects performing a drill such as Arrowhead or 5-0-5. The measurements may be collected by one or more sensors attached to the body of each subject, as detailed in steps 612, 616, 624 and 625 below and in association with FIGS. 7A-7F below. Each such data may be associated with a label indicating how fast the relevant subject performed the drill. Additionally, or alternatively, a label can be provided by a professional human, or by an automated system to estimate the technique and/or effort during the entire drill or each turn.

On step 604, the parameters associated with the drills may be provided for training to an AI engine trainer, together with the time label associated with each such drill.

The AI engine may be trained upon the data and the labels, to obtain a trained engine 607.

On step 608, when the engine is trained, raw data may be collected for a subject. The data may be obtained as detailed above, from one or more sensors attached to the subject's body.

On step 616, strides may be detected from the raw data, and on step 616 the strides may be classified by stride classifier 612, as detailed above.

On step 624, the strides may be further analyzed, for example by action detector 620, to obtain stride sequences characterizing a certain action such as a turn, as detailed above.

On step 625, the action parameters relevant to the detected action may be retrieved.

For example, the parameters may be retrieved from the raw data collected form the sensors attached to the subject and related to the time in which the action was performed, or from further processing thereof.

On step 628, the data relevant to the detected actions, such as parameters extracted from the raw data which relate to the strides constituting the drill, may be provided to AI engine 607 trained upon the training data, to obtain a time prediction, which is equivalent to the subject's agility. If there are multiple drills, such as Arrowhead and 5-0-5, a model can be built for each drill and the predictions of both drills can be aggregated, for example using a weighted average. Alternatively, the same engine can predict both drill performances.

The score of one or more drills may be obtained from the engine and used for further training AI engine 607 on step 604, to update AI engine 607. For example, AI engine 607 may be re-trained every predetermined period of time, when at least a number of actions has been collected, or the like.

The time may be used as is, and/or combined with further analysis results.

For example, on step 632, a session score may be assigned to the subject, indicating for example the subject's agility on a match. The subject's agility may be determined as the highest agility achieved by the subject, the average agility, or any other aggregation of the agility values assigned to different turns during the match.

Figure 6C:
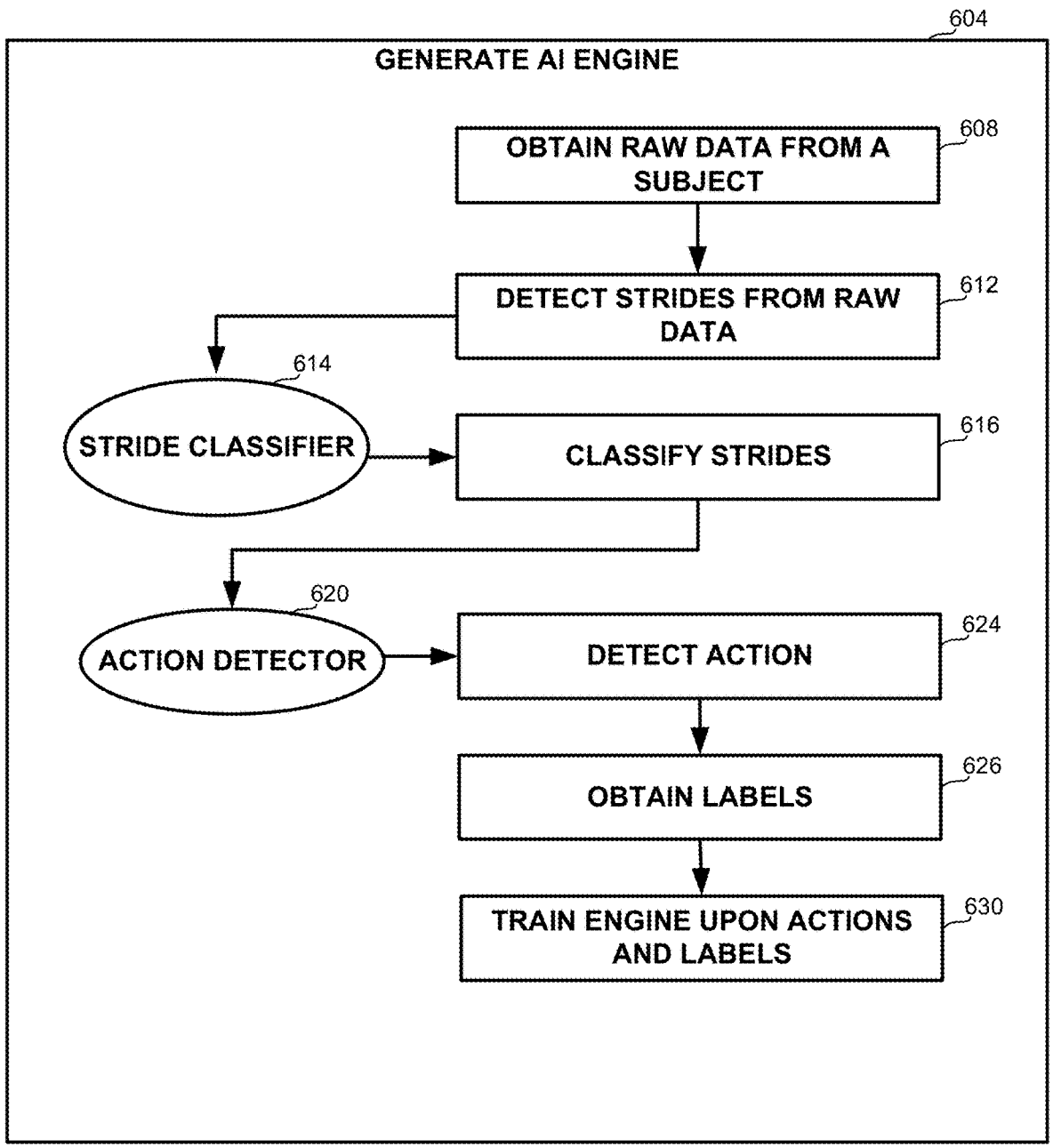
FIG. 6C is a flowchart of steps in a method for generating an AI engine, in accordance with some exemplary embodiments of the disclosure.

Referring now to FIG. 6C, showing a flowchart of steps in a method for training an AI engine, in accordance with some exemplary embodiments of the disclosure.

As detailed in association with FIG. 6A above, on step 608, raw data may be collected for the subject in an uncontrolled environment.

On step 612, strides may be detected from the raw data, and on step 616 the strides may be classified by stride classifier 614.

On step 624, the strides may be further analyzed, for example by action detector 620, to obtain stride sequences characterizing a required action, such as a few steps forward, turn to the right/left, and few additional steps.

On step 626, labels may be obtained for each such action. The labels may be determined arbitrarily, automatically, provided by a human subject, or a combination thereof. The label may be expressed by the time it took to complete the drill which the turn was part of, and/or the effort put by the subject, and/or an assessment of his turning "technique". The time may be determined by an automatic process analyzing the measurements or by processing one or more images of the subject performing the action. The effort can be estimated by one or more other measurement systems such as force platform, electromyography, or the like. The technique and/or effort may be estimated by a practitioner analyzing the subject's motion, legs control or angles, or the like, or automatically using a database containing large set of subjects performing this drill.

On step 630, an AI engine may be trained upon the data and the labels, using for example an AI engine trainer, to obtain a trained engine 606.

Figure 7A:
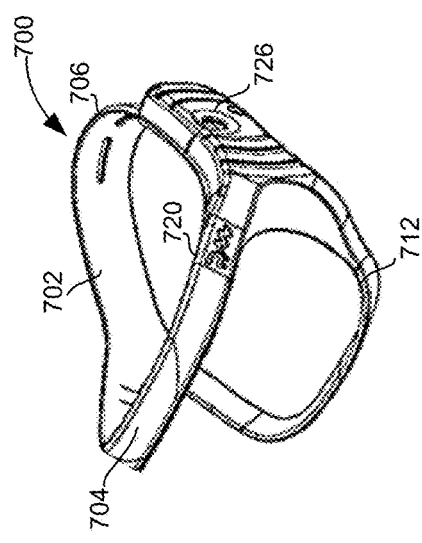
FIGS. 7A and 7B show two views of a footwear sensor unit, in accordance with some exemplary embodiments of the disclosed subject matter.
Figure 7B:
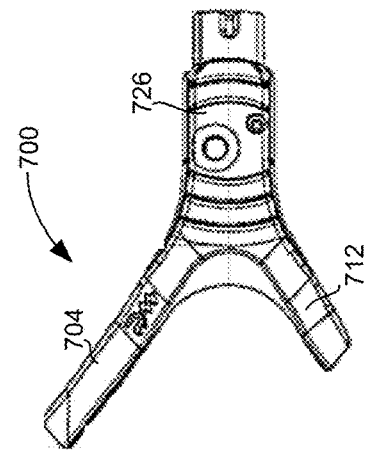
Figure 7C:
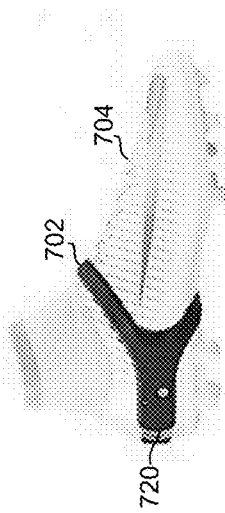
FIG. 7C shows a shoe having mounted thereon the footwear sensor unit, in accordance with some exemplary embodiments of the disclosed subject matter.
Figure 7D:
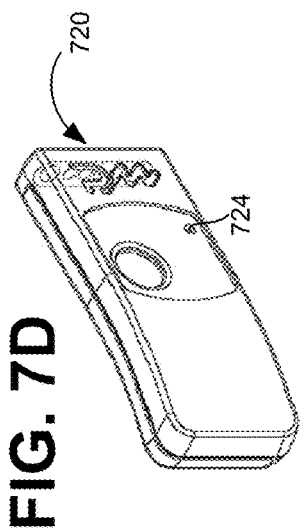
FIGS. 7D-7F show various views of an exemplary housing for a motion sensor, in accordance with some exemplary embodiments of the disclosed subject matter.
Figure 7E:
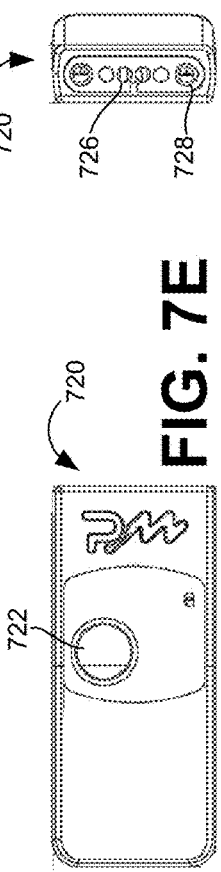
Figure 7F:
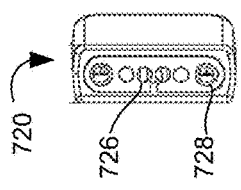

Referring now to FIGS. 7A and 7B showing two views of a footwear sensor unit 700, to FIG. 7C, showing a shoe 704 having mounted thereon footwear sensor unit 700, and to FIGS. 7D-7F showing an exemplary housing or casing for a motion sensor to be mounted on a shoe.

FIG. 7C depicts a footwear sensor unit 700 mounted on a shoe 704. Footwear sensor unit 700 includes a motion sensor module within a housing 720 and a mounting strap 702. Housing 720 and mounting strap 702 are alternatively referred to herein as a mounting system. Housing 720 may be made of plastic material, while mounting strap 702 may be elastic. Housing 720 may encase a motion sensor, such as a 6 degrees of freedom (DOF) motion sensor, for example an MPU-9150™ made by InvenSense headquartered in San Jose, Calif., USA. The product specification of the MPU-9150™ is incorporated by reference in its entirety and for any purpose. It will be appreciated, however, that the MPU-9150™ is merely an exemplary IMU and that any 6- or 9-DOF or other similar motion sensor can be used. In some embodiments, the motion sensor is a 9-DOF motion sensor of which the system only utilizes sensor data from a 3-axis gyroscope and a 3-axis accelerometer, i.e., only 6-DOF.

Housing 720 may be inserted into a compartment on elastic strap 702. Strap 702 may be mounted on soccer shoe 704.

Strap 702 may be made of any resilient, flexible and elastic material that can be stretched and flexed into place on shoe 704 and withstand the rigors of running, kicking a ball, contact with other players, or the like, while remaining securely in place and not snapping. Strap 702 and housing 720 may be made of rugged, heavy-duty material that is needed to withstand the constant rubbing against the ground (under-strap) and numerous impacts from the soccer ball and other objects such as other players' feet.

Housing 720 may comprise a sensor board, e.g., a printed circuit board (PCB) with components such as the IMU and electronic components. Housing 720 may be designed to keep the PCB safe from any impact it might endure during a match or a training session. Furthermore, the design of strap 702 may place housing 720 in a "ball-free shoe zone", where the ball is least likely to hit housing 720. Thus, housing 720 may be mounted such that it does not interfere with the way the ball is kicked on one hand, and is not damaged on the other hand. Moreover, strap 702 may be designed in such a manner that all foot movement is directly transferred to the motion sensor as if the foot and the sensor unit formed a single body.

FIGS. 7A and 7B illustrate an exemplary mounting strap 702. Mounting strap 702 may be formed as a single piece of material that includes a back-strap 706, an upper strap 704 and a lower strap 712. Back strap 706 may be U-shaped where the open ends of the U split into upper strap 704 and lower strap 712, both of which make closed circuits of their own. Back strap 706 is adapted to be fitted around the heel of a boot while the front of the boot slips between the upper strap 704 and lower strap 712. Upper strap 704 is adapted to lie across the top rim or near the top rim of the upper of the shoe where the shoe covers the foot, and to cover the part of the shoelaces near the tongue of the shoe. Lower strap 712 may be adapted to be fitted under the bottom of the shoe and to traverse the sole of the boot across an area of the sole which is devoid of cleats (studs). The design, flexibility and elasticity of the mounting strap ensure that the strap is held tightly in place, without shifting position. In embodiments, the strap is adjustable and may or may not form a closed circuit, i.e., two ends of the strap may be open. In other embodiments, the strap is not adjustable. Straps may come in different sizes and can be matched to a given shoe size. The straps can include some or all of the elements described above.

Both right- and left-hand mounting straps may be provided. For a right shoe, the mounting strap may include a holding pouch 726 on the right-hand prong of the U of back strap 706 as viewed from behind the strap and above. For a left foot shoe, holding pouch 726 may be located on the left prong of the U when viewed as above.

FIGS. 7D, 7E and 7F illustrate an exemplary housing 720 for motion sensor 700. Housing 720 may be removably insertable into pouch 727 of strap 702. In the depicted embodiment, housing 720 may include a button aperture 722 via which an operator can actuate the button that activate the motion sensor unit. The casing may further comprise an opening 724 through which one or more LED indicators can be seen. The lights may indicate the status of the motion sensor unit. Other embodiments of the housing may or may not include the same or similar apertures and may or may not have alternative or additional apertures and/or structural elements.

In the depicted embodiment, housing 720 may further include power contacts/ports and/or data ports 728. For example, ports 728 may be power ports for charging a rechargeable battery of the sensor unit and contacts 726 may be data ports for transferring raw or calculated sensor data via a physical medium. Alternatively, ports 728 may be used for data transfer while contacts 726 may be used for charging the unit. In other embodiments, one or more apertures within housing 720 may be used for securing the housing in place while the battery draws charge via contacts 726. The foregoing configurations are merely exemplary and it is made clear that any configuration for charging and/or transferring data is included within the scope of the invention.

Further details of the structure and operation of sensor unit 700 are provided in US Patent Application Publication no. US2020/0229762 published Jul. 23, 2020, incorporated herein by reference in its entirety and for all purposes.

Additionally or alternatively, sensory data may be obtained from a motion capture system, such as a camera, a video camera, or the like.

It will be appreciated that the disclosed mounting straps and housing are exemplary only, and that the sensors(s) may be installed anywhere, for example within the shoe sole, on another part of the shoe, as part of another garment such as a sock, or on another part of the user's body, such as the head, hand, torso, lower back, thighs, calves, or the like.

Figure 8:
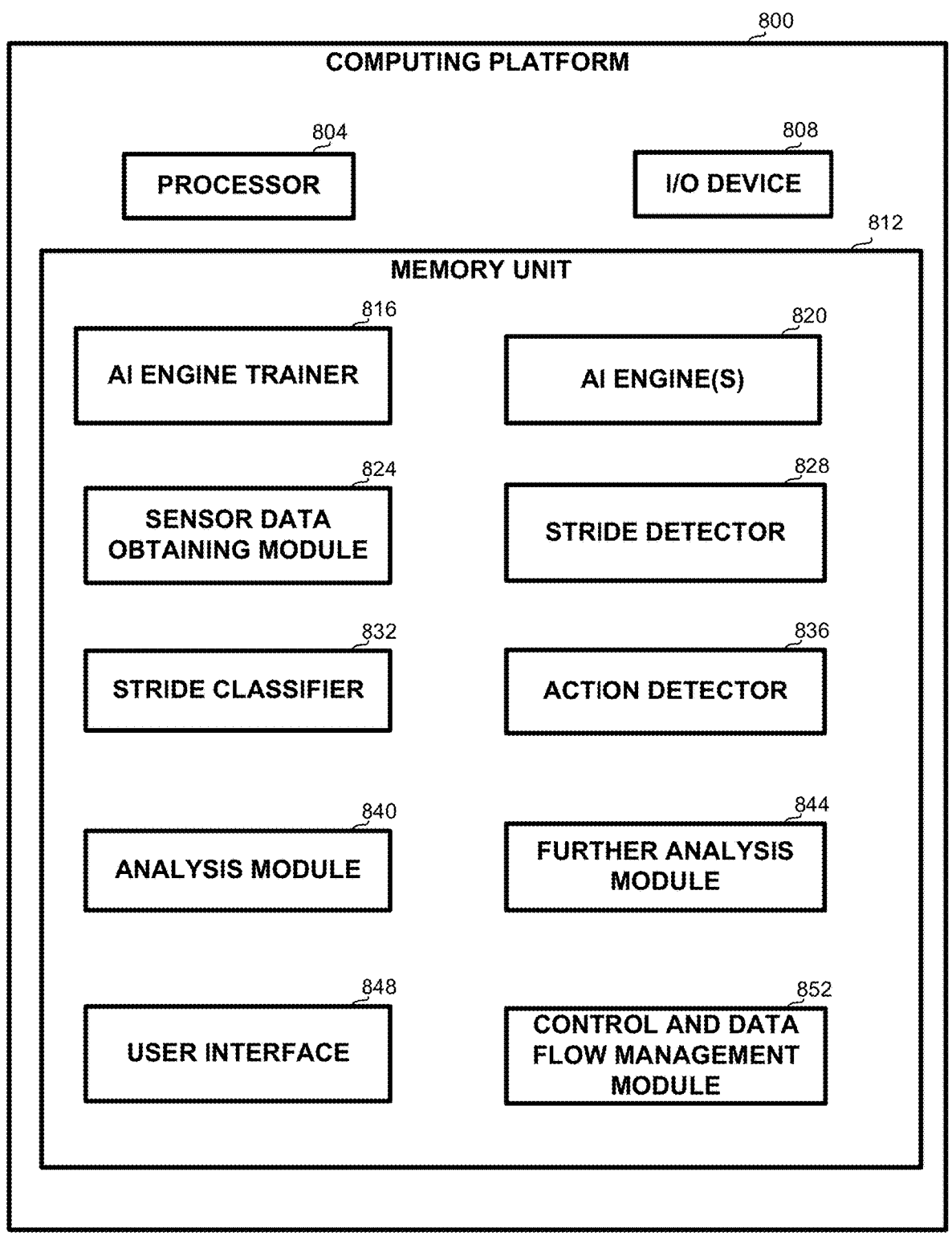
FIG. 8 is a block diagram of a computing platform for assessing performance, in accordance with some exemplary embodiments of the disclosed subject matter.

Referring now to FIG. 8, showing a block diagram of a computing platform 800 for assessing performance, in accordance with some exemplary embodiments of the disclosed subject matter.

It will be appreciated that one or more of the components detailed below may be executed by a remote processor communicating with computing platform 800, such as a remote server. In the discussion below the term "user" may relate to an individual examining the performance of a subject, such as the subject himself, a coach, a physician or the like.

In some exemplary embodiments computing platform 800 may comprise a processor 804, which may be a Central Processing Unit (CPU), a microprocessor, an electronic circuit, an Integrated Circuit (IC) or the like. Processor 804 may be utilized to perform computations required by computing platform 800 or any of its subcomponents. Processor 804 may be configured to execute computer-programs useful in performing the methods of FIG. 6 above.

In some exemplary embodiments, one or more I/O devices 808 may be configured to receive input from and provide output to a user. In some exemplary embodiments, I/O devices 808 may be utilized to present to the user a user interface, obtain user definitions, and display the results such as the graphs shown in FIGS. 1-3 above. I/O devices 808 may comprise a display, a keyboard, a mouse, a touch screen or another pointing or tracking device, a speakerphone, a microphone, a voice activated module, or the like.

In some exemplary embodiments, computing platform 800 may comprise a memory unit 812. Memory unit 812 may be a short-term storage device or long-term storage device. Memory unit 812 may be a persistent storage or volatile storage. Memory unit 812 may be a disk drive, a Flash disk, a Random Access Memory (RAM), a memory chip, or the like. Memory unit 812 may be a single memory device, or multiple interconnected memory devices which may be co-located or located in different locations and communicating via any communication channel. Memory unit 812 may retain one or more databases, AI engines, or the like.

In some exemplary embodiments, memory unit 812 may retain program code operative to cause processor 804 to perform acts associated with any of the subcomponents of computing platform 800. In some exemplary embodiments, memory unit 812 may retain program code operative to cause processor 804 to perform acts associated with any of the steps shown in FIG. 6 above.

The components detailed below may be implemented as one or more sets of interrelated computer instructions, executed for example by processor 804 or by another processor. The components may be arranged as one or more executable files, dynamic libraries, static libraries, methods, functions, services, or the like, programmed in any programming language and under any computing environment.

Memory unit 812 may retain AI engine trainer 816, for receiving input data comprising one or more data points and a corresponding label to each data point. In some embodiments, each data point may comprise values of parameters relevant to the action, and the label may be time, effort, or the like.

Memory unit 812 may retain one or more AI engines 820 as trained by AI engine trainer 816. Each such AI engine may receive a data point, similar to the data points that used to train the AI engine, and output a prediction. In some embodiments, one AI engine may output two or more predictions, such as time and effort of a turn, while in other embodiments, two engines may be trained, each predicting a single output.

Memory unit 812 may retain sensor data obtaining module 824, for receiving sensor data from one or more sensors as described in association with FIGS. 7A-7F above.

Memory unit 812 may retain stride detector 828 for detecting one or more strides within the sensory raw data received by sensor data obtaining module 824.

Memory unit 812 may retain stride classifier 832 for classifying the strides detected by stride detector 828.

The operation of stride detector 828 and stride classifier 832 is further detailed in U.S. Pat. No. 11,006,860 filed Oct. 5, 2020 titled "Method and apparatus for gait analysis", incorporated herein by reference in its entirety and for all purposes.

Memory unit 812 may retain action detector 836 for detecting an action comprised of a sequence of one or more strides of predetermined types.

Once an action is detected, the parameters relevant to the action may be calculated upon the measurements, and provided to AI engine 820, to obtain a prediction.

Memory unit 812 may retain analysis module 840 for analyzing the predictions obtained by applying one or AI engines for one or more sets of parameters. For example, the analysis may comprise recommendations for a specific training program, for rest, or the like.

Memory unit 812 may retain advanced analysis module 844 for performing advanced analysis of the obtained prediction with or without additional data. For example, the advanced analysis may comprise potential analysis, comparison of the performance of two or more subjects, aggregated performance of one or more subjects over a period of time, or the like.

In some embodiments, analysis module 840 and advanced analysis module 844 may be implemented as a single analysis module.

Memory unit 812 may retain user interface 848 for receiving instructions or preferences from a user, and providing information to the user, for example over I/O device 808 such as displaying graphs, showing recommendations, or the like.

Memory unit 812 may retain data and control flow management module 852 for activating and managing the control flow between the various modules, obtaining and providing the data required for each module, or the like.

The disclosure thus provides for a method for scoring the performance of a subject according to a predetermined metric associated with a controlled environment, based on kinematic measurements collected in an uncontrolled environment. The score may be obtained form a trained AI engine.

In some embodiments, the label and the score of the AI engine may relate to the agility of the subject, which may be determined upon the time it took the subject to perform the drill and/or the quality The quality may be related to the turning technique and be assessed by a professional observer during the training. Additionally or alternatively it may measure the subject effort, in this case during training of the system, the effort/load can be measured using other devices such as force plates. In other embodiments, the score may relate to height in drills of high jumping, weight in drills of weightlifting, completion time, segment time, distance, frequency, maximal velocity, symmetry, or other parameters of the action to be scored.

The subject's biomechanical measurements may be analyzed to detect relevant events or actions in an uncontrolled environment. The action components may then be projected on the studied drill(s) to provide a score.

In some embodiments, advanced analysis may take place, including for example scoring over a period of time, such as a game, a session, a season, or the like, based on multiple actions.

In some embodiments, the effort over a period of time may be aggregated to obtain a "load score", e.g. a total effort. The total effort may be indicative of an injury risk and may thus be useful in planning the training for a player, selecting strategies for matches, or the like.

In some embodiments, a potential score may be assessed, using for example extrapolation based on the measured events, to predict the best performance the subject may achieve in the drill.

The predictions may be updated over time, using the data collected for one or more events, training results or the like.

The disclosure thus provides a methodology for technique and load estimation and monitoring over time, based on a benchmark built upon multiple parameters defining the events.

The disclosure further provides for visualizing this estimation, to allow for easily monitoring the subject's performance, including for example changes over time due to improved technique, inferior technique due to injury or fatigue, comparing to other players and to general benchmarks, setting personal goals, or the like. The actions occurring during a session or a period may be visually presented to illustrate the load level and/or technique and/or quality and to define the focus of desired training, show a typical or optimal action distribution for a player based on his position.

The disclosure may also be used for assessing the performance, advancement, or the potential of individuals such as young sportsmen, for example relative to benchmarks, in order to identify talents, and determine how to best promote them.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as Python, MATLAB, the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. An apparatus comprising:
a motion sensor configured to be mounted on a shoe of a subject;
and a processor, the processor being adapted to perform the steps of:
receiving a model associating motion parameters of an action performed by the subject with a score, the model based at least partially on values of the motion parameters obtained in a controlled environment while performing a task on a first time period;

receiving data output from the motion sensor;

responsive to the received data, determining action parameters during motion of the subject within an uncontrolled environment on a second time period, the motion of the subject within the uncontrolled environment being part of an activity that is different than the first task;

inputting the action parameters into the model, to obtain an assessment of an expected score for the subject performance of the task as would be performed by the subject in the controlled environment; and displaying the assessment of the expected score on a display, wherein the model comprises an artificial intelligence (AI) engine.

2. The apparatus of claim 1, further comprising:

a housing, the motion sensor secured to the housing; and a mounting strap, the housing secured to the mounting strap, wherein the mounting strap is configured to be mounted on the shoe of the subject.

3. The apparatus of claim 1, wherein the processor is further adapted to estimate an aggregate score for the subject performance of a plurality of actions during the second time period.

4. The apparatus of claim 1, wherein the processor is further adapted to estimate a potential score for the subject performance of the task in the controlled environment.

5. The apparatus of claim 1, wherein the data output from the motion sensor comprises kinematic raw data of the subject, and wherein determining the action parameters during motion comprises:

detecting at least one stride within the motion based on the kinematic raw data;

classifying the at least one stride to obtain a stride class;

identifying a sequence of strides complying with a stride class combination; and determining the action parameters in accordance with the kinematic raw data associated with the sequence of strides.

6. The apparatus of claim 1, wherein the score comprises a quality measure.

7. The apparatus of claim 6, wherein the quality measure relates to an effort by the subject, wherein a lower effort indicates higher quality.

8. The apparatus of claim 1, wherein the score comprises at least one measure selected from the group consisting of: power, agility, first step, sprint, speed, jump, endurance and ball control.

9. The apparatus of claim 1, wherein the action is at least one item selected from the group consisting of: turn, jump, accelerate, decelerate, running at constant speed, cut off, maximal speed.

10. The apparatus of claim 1, wherein the task is a drill selected from the group consisting of: Arrowhead, 5-0-5, T-test, lane agility, CMJ, CMJ with arms, pogo jumps, standing vertical leap, max vertical leap, 20 m sprint, 30 m sprint, 40 m sprint, 3-quarter sprint, shuttle run, MAS test, Yo-Yo, and 30-15.

11. The apparatus of claim 1, wherein the expected score is a measure of the task based on at least one metric selected from the group consisting of: completion time, segment time, distance, frequency, maximal velocity, symmetry, height and weight.

12. The apparatus of claim 1, wherein the task is a combination of one or more actions selected from the group consisting of: walking, turning, climbing stairs, sitting and rising, and the score is stability or neurological condition.

13. The apparatus of claim 1, wherein the task is a predetermined drill and the expected score is a time a subject is expected to complete a drill.

14. The apparatus of claim 13, wherein the score is agility, the actions are turns, the controlled-environment tasks are arrowhead and 5-0-5 drills, and the drill time is indicative of agility of the subject.

* * * * *